(12) United States Patent
Manzke et al.

(10) Patent No.: US 8,805,479 B2
(45) Date of Patent: Aug. 12, 2014

(54) METHOD AND A COMPUTER PROGRAM FOR DETERMINING A FUNCTIONAL PROPERTY OF A MOVING OBJECT

(75) Inventors: Robert Manzke, Ulm (DE); Raymond Chan, San Diego, CA (US); Vivek Reddy, Boston, MA (US); Andre Luiz Buchele D'avila, Boston, MA (US)

(73) Assignees: Koninklijke Philips N.V., Eindhoven (NL); The General Hospital Corp., Boston, MA (US)

( * ) Notice: Subject to any disclaimer, the term of this patent is extended or adjusted under 35 U.S.C. 154(b) by 1160 days.

(21) Appl. No.: 12/526,048

(22) PCT Filed: Feb. 7, 2008

(86) PCT No.: PCT/IB2008/050437
§ 371 (c)(1),
(2), (4) Date: Oct. 30, 2009

(87) PCT Pub. No.: WO2008/099304
PCT Pub. Date: Aug. 21, 2008

(65) Prior Publication Data
US 2010/0094128 A1 Apr. 15, 2010

Related U.S. Application Data

(60) Provisional application No. 60/913,549, filed on Apr. 24, 2007, provisional application No. 60/889,793, filed on Feb. 14, 2007.

(51) Int. Cl.
*A61B 5/05* (2006.01)

(52) U.S. Cl.
USPC ........... 600/427; 600/426; 600/483; 600/508; 600/513; 607/17; 607/18

(58) Field of Classification Search
None
See application file for complete search history.

(56) References Cited

U.S. PATENT DOCUMENTS

| | | | |
|---|---|---|---|
| 5,370,679 A | 12/1994 | Atlee, III | |
| 5,549,650 A | 8/1996 | Bornzin et al. | |
| 6,368,285 B1 | 4/2002 | Osadchy et al. | |
| 6,468,265 B1* | 10/2002 | Evans et al. | 606/1 |
| 6,473,635 B1 | 10/2002 | Rasche | |
| 6,501,981 B1 | 12/2002 | Schweikard | |
| 2003/0100925 A1 | 5/2003 | Pape et al. | |
| 2004/0024421 A1 | 2/2004 | Ideker et al. | |
| 2004/0097806 A1 | 5/2004 | Hunter et al. | |
| 2006/0100509 A1 | 5/2006 | Wright | |
| 2006/0173269 A1* | 8/2006 | Glossop | 600/407 |
| 2006/0190045 A1 | 8/2006 | Marcus et al. | |
| 2006/0276867 A1 | 12/2006 | Viswanathan | |

FOREIGN PATENT DOCUMENTS

WO WO2007017879 2/2007

* cited by examiner

*Primary Examiner* — Unsu Jung
*Assistant Examiner* — Joseph M Santos Rodriguez

(57) ABSTRACT

A system for determining a functional property of a moving object includes a tag contactable to the object such that the tag follows the movement of the object. The system further includes a movement determination device configured to determine the movement of the tag. The system also includes a functional property determination device configured to determine a functional property of the object from the determined movement of the tag.

11 Claims, 3 Drawing Sheets

METHOD AND A COMPUTER PROGRAM FOR DETERMINING A FUNCTIONAL PROPERTY OF A MOVING OBJECT

CROSS REFERENCE TO RELATED CASES

Applicants claim the benefit of International Application Number PCT/IB2008/050437, filed Feb. 7, 2008, and Provisional Applications Ser. Nos. 60/889,793, filed Feb. 14, 2007 and 60/913,549, filed Apr. 24, 2007.

FIELD OF THE INVENTION

The present invention relates to a system, a method and a computer program for determining a functional property of a moving object.

BACKGROUND OF THE INVENTION

In WO 2007/017879 A2 a cardiac resynchronization therapy (CRT) is disclosed, in which pacer electrodes are implanted in cardiac chambers and vessels. The idea of CRT is to improve the cardiac output by pacing the right and the left heart chambers in an optimal way by the pacer electrodes. In order to find the optimal position and adaptation of the pacer electrodes, e.g. a position and an adaptation leading to a synchronized movement of the right and left heart chambers, several adaptations and positions of the electric pacer electrodes have to be tried and for each combination of adaptation and position of the pacer electrodes the degree of cardiac synchrony, in particular of synchrony of the left and right heart chambers, has to be determined. Since the heart tissue and the heart vessels are not visible in an X-ray imaging device, which is generally present during CRT for tracking the position of the pacer electrodes, an additional imaging device is required for determining the above mentioned functional property of the heart, i.e. the degree of cardiac synchrony. The WO 2007/017879 A2 discloses an ultrasound imaging device as this additional imaging device. The wall of the heart is visible in the ultrasound imaging device and wall motion dynamics can be determined from the images of the ultrasound imaging device for determining the degree of cardiac synchrony. The need for an additional imaging device to image the heart during CRT makes the system complex and more expensive.

It is therefore an object of the present invention to provide a system, a method and a computer program for determining a functional property of a moving object, without the need for direct imaging of the object itself.

In a first aspect of the present invention a system for determining a functional property of a moving object is presented, wherein the system comprises:
- a tag contactable to the object such that the tag follows the movement of the object,
- a movement determination device for determining the movement of the tag, and
- a functional property determination device for determining a functional property of the object from the determined movement of the tag.

The invention is based on the idea that, since the system only needs the ability to determine the movement of the tag, the movement of the object itself does not need to be directly interrogated by the movement determination device. The tag can be selected such that the movement of the tag can easily be determined by the movement determination device. Since the tag is contactable to the object such that the tag follows the movement of the object, the determined movement of the tag is correlated to the movement of the object and, thus, the functional property determination device can determine a functional property of the object from the determined, in particular, quantified, movement of the tag. Therefore, the system in accordance with the present invention allows for determination of a functional property of the object without the need for determining the movement of the object directly, in particular without the need for direct imaging of the object in question. A functional property of the object can therefore be determined, even if the movement of the object itself cannot directly be determined, in particular even if the object itself cannot be visualized by an imaging device.

The movement of the tag is preferentially represented by a motion vector or a motion vector field and the functional property is preferentially determined from the motion vector or the motion vector field, respectively.

The object is preferentially a moving organ like a human heart, wherein the tag is contactable to the moving organ such that the movement follows the movement of the object. In particular, the object is preferentially a heart muscle and/or a heart chamber and further preferred a moving wall of a heart muscle or a heart chamber.

In general, the determined movement of the tag is caused by a movement of the object being a real absolute or relative movement of the whole object or of at least a part of the object, but the determined movement can also be a zero movement, i.e. the determination device could also determine that the tag is not moving at all.

The tag is selected such that the movement of the tag can be determined by the movement determination device. The movement determination device includes preferentially an X-ray imaging system, for example, an X-ray fluoroscopy system being, for example, a simple X-ray projection imaging system, a computed tomography imaging system or an X-ray C-arm system. In particular, if the movement determination device includes an X-ray imaging system, the tag is selected such that it can be detected by X-rays, i.e. in this case the tag is preferentially a highly X-ray attenuating element, in particular catheters, wires, electrodes or leads comprising metallic elements. The motion determination device preferentially tracks the tag temporally and spatially in order to determine the movement of the tag.

In a preferred embodiment, the system comprises a plurality of tags, wherein the movement determination device is adapted for determining the movement of several tags and wherein the functional property determination device is adapted for determining one or several functional properties from the determined movements of the tags. If the system comprises several tags, the tags can represent more accurately the movement of the object and, thus, one or several functional properties of the object can be determined more accurately, in particular if different parts of the object move differently.

The tag can be attached to the object and/or it can abut the object such that there is a continuous contact between the object and the tag at least during a predetermined time interval. Preferentially, the tags are implanted in the object.

The functional property determination device can be adapted for determining only one functional property or for determining several functional properties from the determined movement of the tag or from the determined movements of the tags.

It is further preferred, that the movement determination device is adapted for determining a temporal, i.e. time-dependent, image of the tag and for determining the movement of the tag from the temporal image. This image-based determination of the movement of the tag, i.e. the tracking of the tag, can be performed by any appropriate method, for example, snake-based, vessel-filter based, correlation-based, template-based or the like.

In a preferred embodiment, the functional property determination device is adapted for determining a movement of the object from the determined movement of the tag and for determining the functional property of the object from the determined movement of the object. Since the functional property of the object, which is determined by the functional property determination device, depends on the movement of the object, the determination of the functional property directly from the determined movement of the object further improves the degree of accuracy of the determined functional property.

It is preferred that the moving object is a first object within a second object, wherein the tag is insertable into the second object for contacting the tag to the first object such that it follows the movement of the first object. This allows determining of a functional property of a moving object, even if the moving object is located within a second object. The first object is, in particular, a human heart located within a patient being the second object. In particular, this allows determining a functional property of a human organ, like a human heart.

It is further preferred that the moving object is a moving heart, wherein at least one first tag is contactable to the right chamber of the heart, wherein at least one second tag is contactable to the left chamber of the heart, wherein the movement determination device is adapted for determining a movement of the at least one first tag and of the at least one second tag. This allows determining a functional property of the heart, which is correlated with the movement of the right chamber and the left chamber of the heart, in particular cardiac synchrony and/or cardiac output. It is further preferred that the system comprises at least one third tag, which is contactable to an atrium of a human heart, in particular to the right atrium of a human heart, wherein the movement determination device is adapted for determining a movement of the at least one third tag. This allows determining a functional property of the heart, in particular the cardiac synchrony and/or the cardiac output, from a movement of the at least one third tag, and in particular, in addition, from the movement of the at least one first tag and the at least one second tag.

It is further preferred that the functional property determination device is adapted for determining the movement of the right chamber of the heart from the at least one first tag and the movement of the left chamber of the heart from the at least one second tag. Since the functional property determined by the functional property determination device is correlated with the movement of the heart, the determined movements of the right chamber and the left chamber of the heart can be used for determining the function& property of the heart more accurately.

It is preferred that the functional property determination device is adapted for determining a degree of synchrony between the movement of the right chamber and the left chamber of the heart from the determined movement of the at least one first tag and the at least one second tag and, in particular, from a determined movement of at least one third tag contacted to an atrium of the heart. The degree of synchrony can be used in a CRT. Thus, the determination of the degree of synchrony allows controlling an adaptation and/or a positioning of pacer electrodes during a CRT such that the degree of synchrony is maximized. This is preferentially performed by firstly determining the movement of the heart chambers from the determined movement of the tags and secondly by determining the degree of synchrony from the determined movement of the heart chambers. But, it is also preferred that the degree of synchrony is determined directly from the determined movement of the tags.

It is further preferred that the functional property determination device is adapted for determining a degree of cardiac synchrony including the synchrony between the movement of the right chamber and the left chamber of the heart from the determined movement of the at least one first tag, of the at least one second tag and of at least one third tag, which is contacted to an atrium of the heart, in particular to the right atrium of the heart. Also this degree of cardiac synchrony can be used in a CRT.

It is further preferred that the functional property determination device is adapted for determining a cardiac output from the determined movement of the at least one first tag and the at least one second tag and, in particular, from a determined movement of at least one third tag contacted to an atrium of the heart. Also the determined cardiac output can be used for adapting and positioning pacer electrodes in a CRT such that the properties and positions of the pacer electrodes are optimized, i.e., in this case, that the cardiac output is optimized.

Also the cardiac output can be determined by firstly determining the movement of the heart chambers from the movement of the tags and by secondly determining the cardiac output from the determined movement of the heart chambers. In another embodiment, the cardiac output can be determined from the degree of synchrony of the left and the right heart chambers.

It is further preferred that the system comprises a movement influencing element for influencing the movement of the object. Movement influencing elements are separate elements and/or at least one tag is a movement influencing element. Preferentially, the moving influencing element is a pacing element for pacing a heart, in particular the above mentioned pacer electrode.

Preferentially, the system further comprises an adaptation device for adapting the moving influencing element such that the determined functional property of the object is maximized. For example, if the moving influencing element is a pacing element for pacing a heart, the adaptation device preferentially modifies the amperage and/or the frequency of a current for pacing a human heart such that the determined functional property, which is preferentially a degree of cardiac synchrony, in particular of synchrony of the left and right heart chambers, in particular of the left and right heart chamber contractions, and/or a cardiac output, is maximized.

It is further preferred that the system further comprises a positioning device for positioning the moving influencing element such that the determined functional property of the object is maximized. If the moving influencing element is a pacing element for pacing a human heart, the pacing elements are preferentially positioned such that the determined functional property, which is preferentially a degree of cardiac synchrony, in particular of synchrony of the left and right heart chambers, in particular of the left and right heart chamber contractions, and/or the cardiac output, is maximized.

In a preferred embodiment, the movement influencing element is changeable at least between a first influencing condition and a second influencing condition, wherein the movement determination device and the movement influencing elements are controllable such that a first movement of the tag is determined if the movement influencing element is in the first influencing condition and that a second movement of the tag is determined if the movement influencing element is in the second influencing condition, and wherein the functional property determination device is controllable such that the functional property is determined at least twice, one time from the first movement of the tag and another time from the second movement of the tag, in order to determine the influence of the movement influencing element on the functional property of the object. Preferentially, the first influencing condition is a condition, in which the movement influencing element is activated, and the second influencing condition is preferentially a condition, in which the movement influencing element is deactivated. This allows determining the influence of different conditions of the moving influencing element on the functional property of the object.

It is further preferred that the system comprises a visualization unit for visualizing the determined functional property of the object simultaneously with a visualization of the tag. This gives a user a visualization of a correlation between a position of the tag and the determined functional property. It is preferred that different movements of the tag for example, in different directions or in different velocity ranges, are indicated by different colors.

In a further aspect of the present invention a method for determining a functional property of a moving object is presented, wherein the method comprises:

providing a tag contacted to the object such that the tag follows the movement of the object,
determining the movement of the tag,
determining a functional property from the determined movement of the tag.

In further aspect of the present invention a computer program for determining a functional property of a moving object is determined, wherein the computer program comprises program code means for causing a system as described to carry out the steps of the method as described, when the computer program is run on a computer controlling the system.

It shall be understood that the system, the method and the computer program have similar and/or identical preferred embodiments as defined in the dependent claims. it shall be understood that preferred embodiments of the invention can also be any combination of the dependent claims.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
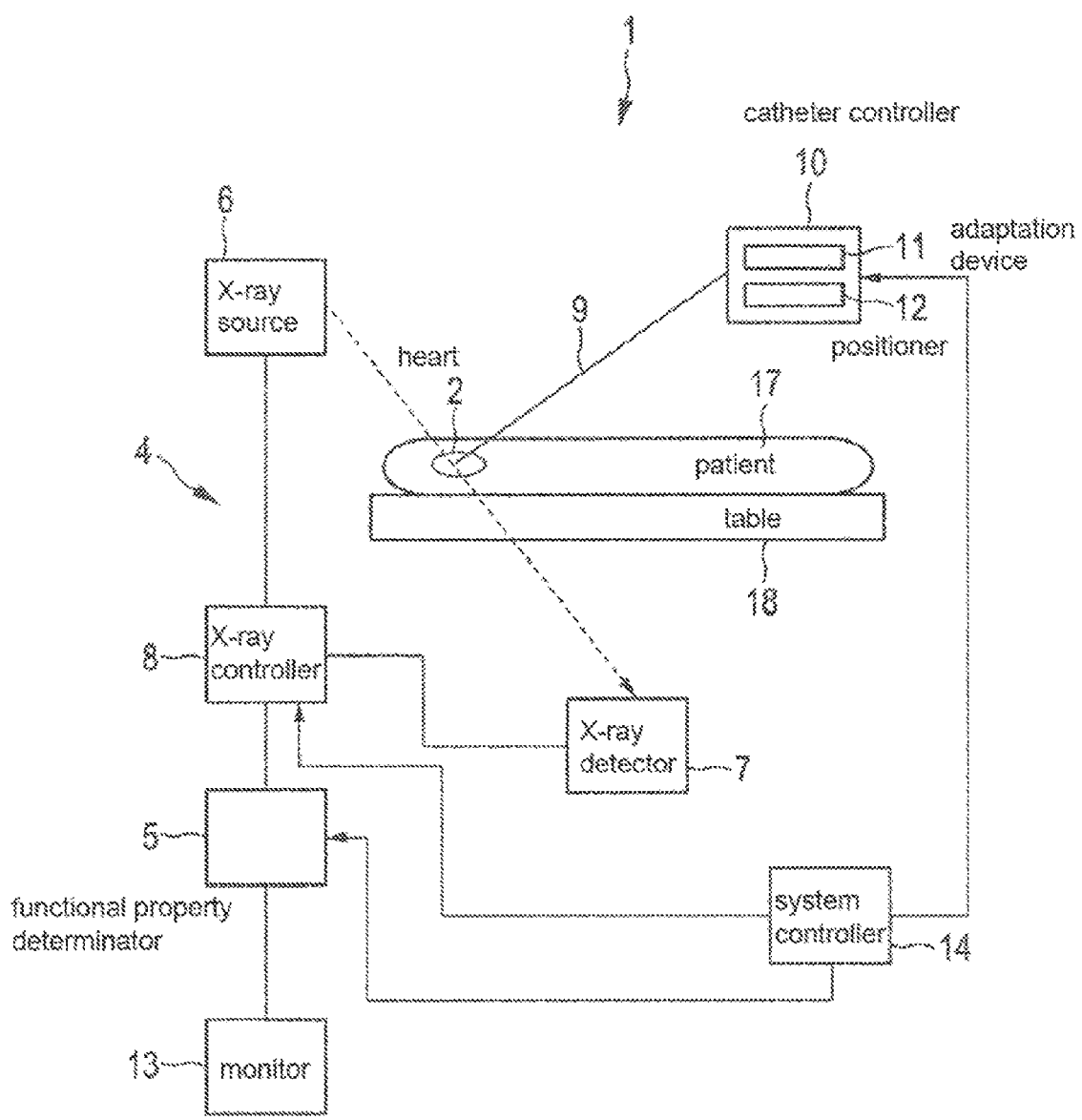
FIG. 1 shows schematically an embodiment of a system for determining a functional property of an object.
Figure 2:
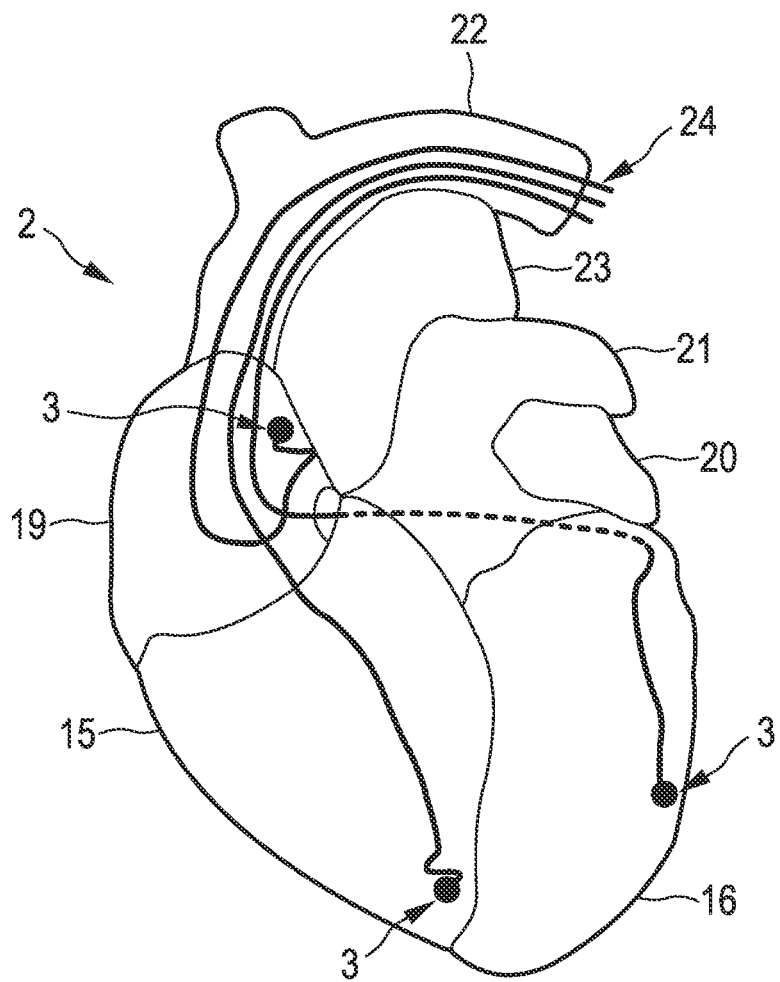
FIG. 2 shows schematically an object and tags of the system, which are contacted to the object for determining a functional property of the object.

FIG. 1 shows schematically a system 1 for determining a functional property of a moving object 2, which is, in this embodiment, a human heart of a patient 17. The patient 17 is located on a patient table 18. A catheter 9 comprising movement influencing elements 3, which are, in this embodiment, pacer electrodes 3, is inserted into the patient 17, wherein the pacer electrodes 3 are attached to the walls, in particular to the endocardium (inner wall) of the right heart chamber 15, the left heart chamber 16 and the right atrium 19, as it is schematically shown in FIG. 2. The pacer electrodes 3 are tags, which are attached and, therefore, contacted to the walls of the right heart chamber 15, the left heart chamber 16 and the right atrium 19 such that they follow the movement of these walls.

In FIG. 2, a human heart is schematically shown. In FIG. 2 reference sign 20 designates the left arterial appendage, reference sign 21 designates the pulmonary trunk, reference sign 22 designates the inferior vena cava and reference sign 23 designates the aorta.

The system 1 further comprises a movement determination device 4 including, in this embodiment, an X-ray projection device 6, 8, 7 for imaging the tags 3 spatially and temporally. The movement determination device is adapted for determining the movement of the tags 3 from fluoroscopic X-ray projection images showing the tags 3. The X-ray projection device comprises an X-ray generation source 6, an X-ray detection unit 7 and a control unit 8 for controlling the X-ray projection device and for determining the movement of the tags 3 from the X-ray projection images. The two functions of the control unit 8, i.e. controlling the X-ray projection device and determining the movement of the tags from the X-ray projection images, can, in other embodiments, be performed by two separate units, a first unit for controlling the X-ray projection device and a second unit for determining the movement of the tags from the X-ray projection images.

The X-ray projection device images, as already mentioned above, the pacer electrodes 3, and the control unit 8 for controlling the X-ray projection device 4 determines the movement of the pacer electrodes 3 from the image of these electrodes 3. In particular, the control unit 8 determines motion vector fields representing the movement of the pacer electrodes 3.

The system 1 further comprises a catheter control unit 10 for controlling the catheter 9 and the pacer electrodes via electrical leads 24, wherein, in this embodiment, the pacer electrodes are the tags 3. In particular, the catheter control unit 10 comprises an adaptation device 11 for adapting the pacer electrodes 3, in particular the amperage and frequency of the current, and a positioning device 12 for positioning the pacer electrodes 3.

The system 1 further comprises a functional property determination device 5 for determining a functional property of the heart 2 from the determined movement of the pacer electrodes 3, i.e. from the determined motion vector fields representing the movement of the pacer electrodes 3. The functional property determination device 5 is preferentially adapted such that a degree of cardiac synchrony, in particular the degree of synchrony between the movement of the right chamber and the left chamber of the hearts is determined from the motion vector fields of the pacer electrodes. Furthermore, preferentially also the cardiac output is determined from the motion vector fields of the pacer electrodes 3.

The determined functional properties are visualized on a visualization unit 13, like a monitor, which shows the determined functional property simultaneously with the visualization of the pacer electrodes 3. In particular, in this embodiment, the visualization unit 13 shows an X-ray projection image of the pacer electrodes 3 overlaid by the determined functional property of the human heart 2, in particular overlaid by the determined degree of a synchrony and cardiac output. This gives a user a direct correlation between the positions of the pacer electrodes 3 and the determined functional properties of the heart. In addition, preferentially also the determined motion vector fields representing the movement of the pacer electrodes 3 are overlaid on the X-ray projection image of the pacer electrodes 3.

The motion vector fields can be determined as absolute or relative two dimensional spatiotemporal displacement of the tags on an X-ray projection. Relative displacement can be measured in between a multitude of tags, between tags tracked throughout several cardiac cycles, between tags which are repositioned during the procedure and/or during modification of a pacing algorithm (for example, pacing on/off). The spatiotemporal displacement and hence the motion vector field can be displayed in a graph or as a color coded overlay on the X-ray image. For example, two tags, located in the right heart chamber and left heart chamber, could be surrounded with green lines, if they move synchronously towards/apart from each other, for example, by contraction, expansion, rotation or ventricular/apical rocking A different color could be used if, for example, the right heart chamber tag starts to move first and is then followed by the LV tag, which indicates delay of activation and hence dyssynchronicity.

The system is controlled by a system control unit 14, which controls the catheter control unit 10, the control unit 8 for controlling the X-ray projection device and for determining the movement of the tags and the functional property determination device 5.

Figure 3:
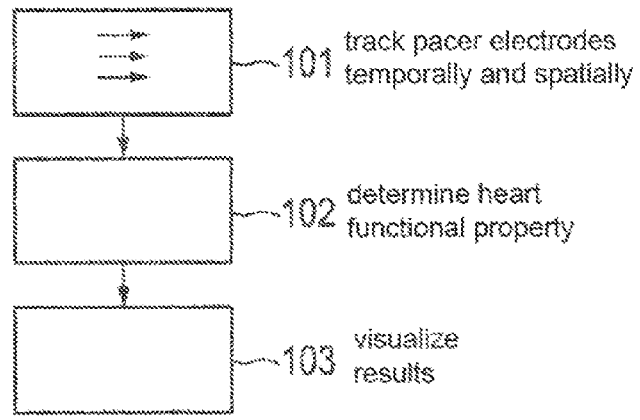
FIG. 3 shows a flow chart illustrating an embodiment of a method for determining a functional property of the object.

In the following, a method for determining a functional property of a moving object in accordance with the invention will be described with reference to a flow chart shown in FIG. 3.

It is assumed that the pacer electrodes 3 are already attached to the left chamber 16 and the right chamber 15 of the heart. In step 101 the movement determination device 4, comprising, in this embodiment, the X-ray projection device, generates fluoroscopic projection images of the pacer electrodes 3 and determines from these generated projection images a movement of the pacer electrodes 3 connected to the left heart chamber 16 and the right heart chamber 15, i.e. the pacer electrodes 3 are temporally and spatially tracked by using the X-ray projection device. The determined movement of the pacer electrodes 3 is represented by motion vector fields, which are transferred to the functional property determination device 5.

The pacer electrodes 3 are preferentially visualized with minimal foreshortening. Thus, if the pacer electrodes 3 have a side, which is longer than the other sides, the radiation source is arranged relative to the pacer electrodes 3 preferentially such that this longer side is located parallel to the rays of the radiation source.

In step 102, the functional property determination device 5 determines from the motion vector field representing the motion of the pacer electrodes 3 a functional property of the human heart 2. In this embodiment, the functional property determination device determines the degree of cardiac, in particular the degree of synchrony of the left heart chamber 16 and the right heart chamber 15 and in addition the cardiac output.

For example, if the tag contacted to the left heart chamber, in particular contacted to the lateral wall of the left heart chamber, and the tag contacted to the right heart chamber, in particular contacted to the septal wall of the right heart chamber, start and end movements at the same time, move with the same speed, in particular over the same distance and towards each other, the functional property determination device 5 determines a high degree of synchrony and, in this embodiment, a high cardiac output. The functional property determination device 5 can consider the movements of the tag over a full cardiac cycle. In this case, the functional property determination device determines a high degree of synchrony and, in this embodiment, a high cardiac output if the tag contacted to the right atrium 19 moves towards the base of the heart 2, if than the tag contacted to the right heart chamber 15 and the tag contacted to the left heart chamber 16 move towards the base (systole), if than the tag contacted to the right atrium 19 moves away from the base and if than the tag contacted to the right heart chamber 15 and the tag contacted to the left heart chamber 16 move away from the base (diastole).

In contrast, for example, if the tag contacted to the right atrium 19 starts to move, if this movement is followed by a movement of the tag contacted to the right heart chamber 15, in particular, contacted to the septal wall of the right heart chamber 15, and if this movement is finally followed by a movement of the tag contacted to the left heart chamber 16, in particular contacted to the lateral wall of the left heart chamber 16, the functional property determination device 5 determines a low degree of synchrony and, in this embodiment, a low cardiac output.

If, in another example, the tag contacted to the right heart chamber 15, in particular contacted to the septal wall of the right heart chamber 15, starts to move at the beginning of the systole, i.e. heart contraction, and if the tag contacted to the left heart chamber 16, in particular contacted to the lateral wall of the left heart chamber 16, starts to move also at the beginning of the systole, but in the same direction as the tag contacted to the right heart chamber 15, the heart is not or only weakly contracting, blood is not or only weakly pushed out of the heart and, thus, the cardiac output is low. This also regarded as low degree of synchrony.

In a further example, the functional property determination device 5 determines a low degree of synchrony, if first the tag contacted to the right heart chamber, in particular contacted to the septal wall of the right heart chamber, moves, if with a time delay also the tag contacted to the left heart chamber, in particular contacted to the lateral wall of the left heart chamber, starts to move in the same direction, i.e. no effective contraction of the heart yet, if than the tag contacted to the left heart chamber moves towards the tag contacted to the right heart chamber, i.e. real contraction, if than the tag contacted to the right heart chamber moves again in the same direction as the tag contacted to the left heart chamber, i.e. no effective contraction, if this is followed by a quiet phase, in which the tags contacted to the left and right heart chamber do not move anymore.

The movement of the pacer electrodes is preferentially tracked over at least one cardiac cycle, in order to determine the functional property over at least one cardiac cycle. An electrocardiogram can be used for assigning a determined movement to a certain cardiac phase, for example, in order to determine the movement in a certain cardiac phase and to compare the movement in a certain cardiac phase with movements of a heart of a healthy person, for example, with an expected contraction (systole) or an expected expansion (diastole).

In step 103, the determined functional properties of the human heart 2, the projection images generated by the X-ray projection device and the motion vector field are transferred to the visualization unit 13, which visualizes the generated projection images being fluoroscopy projection images overlaid by the determined functional properties and preferentially also overlaid by the determined motion vector field. Determined movements in different cardiac phases are preferentially colored by color-kinesis.

Figure 4:
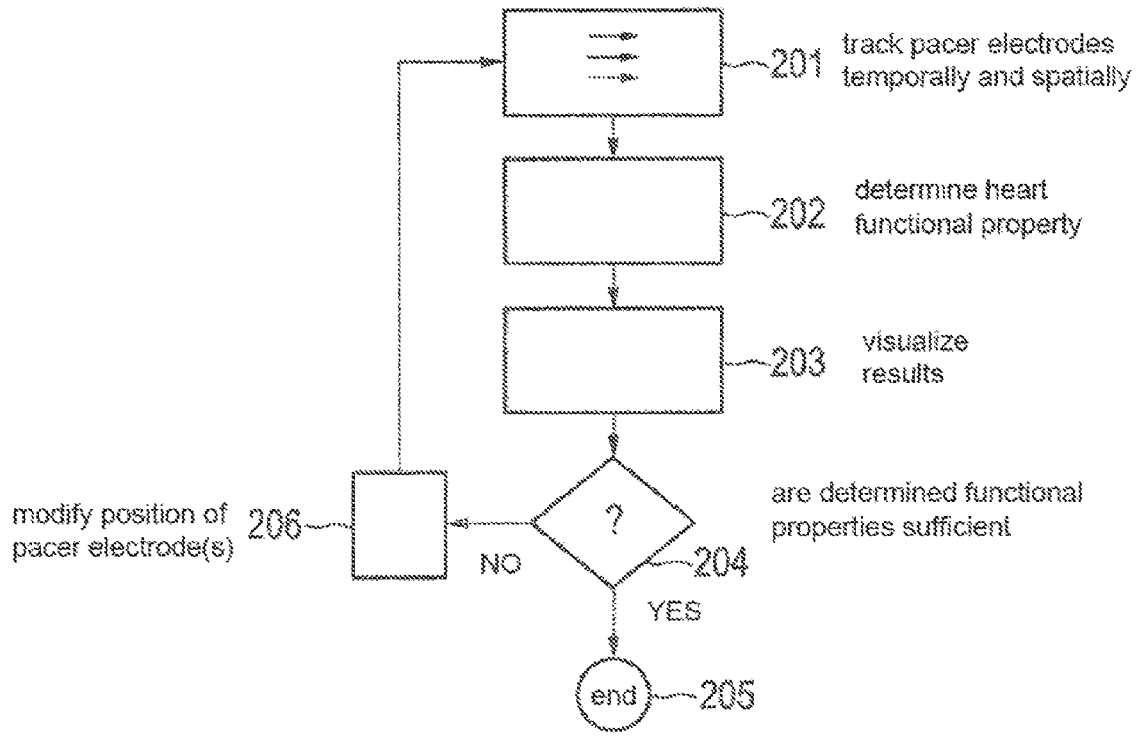
FIG. 4 shows a flow chart illustrating another embodiment of a method for determining a functional property of the object.

In the following another embodiment of a method for determining a functional property of a moving object in accordance with the invention will be described with reference to a flow chart shown in FIG. 4, which does not only allow determining a functional property of an object, but which also allows influencing the functional property of the object.

It is assumed that the pacer electrodes 3 being movement influencing elements are located at initial positions at the left heart chamber 16, the right heart chamber 15 and the right atrium 19 such that they follow a movement of these heart chambers and the right atrium, respectively. In steps 201 to 203 a functional property, in this embodiment the degree of cardiac synchrony, in particular the degree of synchrony of the left heart chamber 16 and the right heart chamber 15, and the cardiac output, are determined from motion vector fields of the pacer electrodes 3 and visualized on the visualization unit 13. Since steps 201 to 203 are similar to steps 101 to 103, for a description of the determination of functional properties of the human heart 2 and their visualization in steps 201 to 203 reference is made to the above given description of steps 101 to 103.

In step 204 it is decided, whether the determined one or several functional properties are sufficient, i.e. e.g. whether the one or several functional properties are above or below a given threshold or within a given range or maximized or minimized depending on the functional property, which has been determined in step 202. In this embodiment, the degree of synchrony of the left heart chamber 16 and the right heart chamber 15, and the cardiac output are determined in step 202. Furthermore, in this embodiment, the degree of cardiac synchrony, in particular the degree of cardiac synchrony and preferentially, the cardiac output have to be maximized. If a maximized degree of cardiac synchrony and, preferentially, a maximized cardiac output have been achieved or if the degree of cardiac synchrony and preferentially the cardiac output are above a predetermined threshold, the method ends in step 205. If a maximal degree of cardiac synchrony and preferentially a maximal cardiac output have not been achieved yet or if the degree of cardiac synchrony and preferentially the cardiac output are not above a given threshold, the method continues with step 206.

In step 206, the position of at least one of the pacer electrodes 3, in particular of one of the pacer electrodes 3 attached to the left heart chamber 16, is modified by the positioning device 12. In other embodiments, alternatively or in addition, also the amperage and/or frequency or other properties of the pacer electrodes can be modified by the adaptation device 11.

After the position of at least one of the pacer electrodes 3 has been modified, steps 201 to 204 are repeated, in order to determine, in this embodiment, the degree of cardiac synchrony and, in particular, the cardiac output for the modified position of the pacer electrodes 3 and in order to decide whether these functional properties now fulfill the condition of step 204. If this is the case, the method ends in step 205. Otherwise, the method continues again with step 206.

In a preferred embodiment, the X-ray projection device generates first temporal projection images, i.e. first fluoroscopic projection images, while the movement influencing elements are in a first influencing condition, and second temporal images, i.e. second fluoroscopic images, while the movement influencing elements are in a second influencing condition. In particular, if the moving influencing elements are pacing elements, like the pacer electrodes, during the first influencing condition the pacing elements are activated, i.e. the pacing elements pace the object, and during the second influencing condition the pacing elements are deactivated, i.e. they do not pace the object. The movement determination device determines a first movement of the tags which corresponds to the first influencing condition and a second movement of the tags which corresponds to the second influencing condition. The first and second movements are preferentially represented by a first and a second motion vector field. The first motion vector field and the second motion vector field are used for determining a first functional property of the object in the first influencing condition and a second functional property in the second influencing condition, in order to determine the influence of the movement influencing elements on the functional property of the object.

The invention can be applied in interventional procedures for determining functional information of organs. This functional information or functional property can be determined, even if only an X-ray imaging device is present, which is not able to visualize the respective organs itself, because, in accordance with the invention, it is only needed to visualize the tags contacted to the organs such that they follow the movement of the organs. But the invention is not limited to a determination of a movement of the tags, which uses X-rays. Also other imaging modalities can be used for determining the movement of the tags, for example, ultrasound or magnetic resonance imaging devices, as long as tags are used, which are visible in the used imaging device.

In a CRT generally pacing elements like pacer electrodes and an X-ray imaging device are used for positioning the pacing elements preferentially at the left and right chambers of the heart. The invention makes preferentially use of these elements, i.e. the pacing elements and the X-ray imaging device, for determining a functional property of the heart, in particular the degree of cardiac synchrony and preferentially cardiac output, without needing further imaging devices.

Instead or in addition to the X-ray projection device described above, a rotational X-ray system can be used to derive more detailed three-dimensional information of the movement of the tags, in particular of the displacement of the tags between a first influencing condition and a second influencing condition. Alternatively or in addition, an X-ray system can be used, which can be wiggled in a controlled fashion, in order to track the tags depth resolved. If the movement of the tags is determined three-dimensionally, the functional property determination unit can be adapted for determining a three-dimensional functional property from the three-dimensional determined movement. The movement of the tags can be determined more accurately, if model information is used, which can be obtained from other functional imaging modalities like an ultrasound imaging device, a magnetic resonance imaging device or a computed tomography imaging device.

The projection images are preferentially acquired in a breath-hold condition. In a further embodiment, a breath motion compensation can be performed, for example, by the control unit 8, in order to obtain a functional property, which is not disturbed by breath movements of the patient, even if the X-ray images are not acquired under breath-hold conditions.

Although in the above mentioned embodiments the movement determination device includes an X-ray imaging device for imaging the tags and for determining the movement of the tags from X-ray images, also other imaging modalities can be used for determining the movement of the tags, as long as the tags are visible in the used imaging modality, for example, the movement determination device can use magnetic resonance imaging devices for determining the movement of the tags.

Although in the above described embodiments the movement of the tags is determined by analyzing the images showing the tags, also another way of tracking the tags can be used for determining the movement of the tags. For example, it is also possible to track the tag by means of a tracking system based on electrical or magnetic fields.

Although in the above described embodiments mainly functional properties of a heart have been determined, the invention can also be used to obtain functional properties from other organs or also from technical objects. The invention can be applied to objects, which are contactable by tags such that the tags follow the movement of the objects, wherein the movement of the tags can be determined by the movement determination unit and wherein a functional property of the object can be determined by the functional property determination device from the determined movement of the tags.

Although in the above described embodiments tags are contacted to the left and right heart chambers and the right atrium, tags can also be contacted to other parts of the heart or only to, for example, the left and right heart chambers.

Although in the above described embodiments the functional property determination device has determined a functional property from motion vector fields representing the movement of the tags, the invention is not limited to a determination of functional properties from motion vector fields. The functional property determination device only needs the spatially and temporally tracked movement of the tags, irrespective of a certain representation of this movement.

Some or all of the above described units or devices can be implemented by one or several units or devices. For example, the control unit 8 and the functional property device 5 can be implemented by only one unit. Furthermore, the units or devices performing calculations and/or determinations like, for example, the part of the control unit 8, which determines the movement of the tags, and the functional property determination device, can be program code means, which perform respective functions and which can run on a computer system, or dedicated hardware, which performs respective functions.

Other variations to the disclosed embodiments can be understood and effected by those skilled in the art and practicing the claimed invention, from a study of the drawings, the disclosure and the appended claims.

While the invention has been illustrated and described in detail in the drawings and in the foregoing description, such illustration and description are to be considered illustrative or exemplary and not restrictive. The invention is not limited to the disclosed embodiments.

In the claims the word "comprising" does not exclude other elements or steps, and the indefinite article "a" or "an" does not exclude a plurality. For example, in claim 1 the system can comprise also two or more tags, which are contactable to the object such that the tags follow the movement of the object. Furthermore, the functional property determination device of claim 1 can be adapted for determining two or more functional properties of the object from the determined movement of the one or more tags.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope of the invention.

The invention claimed is:

1. A system for determining a functional property of a moving object without direct imaging of the moving object itself, the system comprising:
a tag configured to be in direct contact with the moving object such that the tag follows movement of the moving object, wherein the moving object is the heart of a subject;
an imager configured to provide images of the tag;
a movement determination device configured to determine movement of the tag based on the images of the tag; and
a functional property determination device configured to determine the functional property of the moving object from the determined movement of the tag, wherein the functional property is a degree of synchrony between cardiac chambers of the heart or a cardiac output,
wherein the tag comprises an electrode configured to influence the movement of the moving object by electrically pacing the heart, wherein the electrode is changeable at least between a first influencing condition and a second influencing condition, wherein the movement determination device and the electrode are controllable such that a first movement of the tag is determined when the electrode is in the first influencing condition and that a second movement of the tag is determined when the electrode is in the second influencing condition, and wherein the functional property determination device is controllable such that the functional property is determined at least twice, one time from the first movement of the tag and another time from the second movement of the tag, in order to determine the influence of the electrode on the functional property of the moving object.

2. The system as defined in claim 1, wherein the functional property determination device is further configured to determine a movement of the moving object from the determined movement of the tag and to determine the functional property of the moving object from the determined movement of the moving object.

3. The system as defined in claim 1, wherein the moving object comprises a first object within a second object, wherein the tag is configured to be insertable into the second object such that the tag is configured to contact the first object such that the tag follows the movement of the first object.

4. The system as defined in claim 3, wherein at least one first tag is configured to be in contact with the right chamber of the heart, wherein at least one second tag is configured to be in contact with the left chamber of the heart, wherein the movement determination device is further configured to determine a movement of the at least one first tag and of the at least one second tag.

5. The system as defined in claim 4, wherein the functional property determination device is further configured to determine a degree of synchrony between the movement of the right chamber and the left chamber of the heart from the determined movement of the at least one first tag and the at least one second tag.

6. The system as defined in claim 4, wherein the functional property determination device is further configured to determine a cardiac output from the determined movement of the at least one first tag and the at least one second tag.

7. The system as defined in claim 1, further comprising a controller configured to adapt the movement influencing element such that the determined functional property of the moving object is maximized.

8. The system as defined in claim 1, wherein the controller is further configured to position the movement influencing element such that the determined functional property of the moving object is maximized.

9. The system as defined in claim 1, further comprising a monitor configured to visualize the determined functional property of the moving object simultaneously with a visualization of the tag.

10. A method for determining a functional property of a moving object without direct imaging of the moving object itself, the method comprising the acts of:

providing a tag contacted to the moving object, wherein the moving object is the heart of a subject, such that the tag follows movement of the moving object, wherein the tag comprises an electrode configured to influence the movement of the moving object by electrically pacing the heart of the subject, and wherein the electrode is changeable at least between a first influencing condition and a second influencing condition;

obtaining images of the tag using an imager;

determining by a movement determination device movement of the tag based on the images of the tag;

determining by a functional property determination device the functional property of the moving object from the determined movement of the tag, wherein the functional property is a degree of synchrony between cardiac chambers of the heart or a cardiac output;

controlling the movement determination device and the electrode such that a first movement of the tag is determined when the electrode is in the first influencing condition and that a second movement of the tag is determined when the electrode is in the second influencing condition; and controlling the functional property determination device such that the functional property is determined at least twice, one time from the first movement of the tag and another time from the second movement of the tag, in order to determine the influence of the electrode on the functional property of the moving object.

11. A non-transitory computer readable medium comprising computer instructions which, when executed by a processor, configure the processor to determine a functional property of a moving object without direct imaging of the moving object itself by performing the acts of:

providing a tag contacted to the moving object, wherein the moving object is the heart of a subject, such that the tag follows movement of the moving object, wherein the tag comprises an electrode configured to influence the movement of the moving object by electrically pacing the heart of the subject, and wherein the electrode is changeable at least between a first influencing condition and a second influencing condition;

obtaining images of the tag using an imager;

determining by a movement determination device movement of the tag based on the images of the tag; and determining by a functional property determination device a functional property of the moving object from the determined movement of the tag, wherein the functional property is a degree of synchrony between cardiac chambers of the heart or a cardiac output;

controlling the movement determination device and the electrode such that a first movement of the tag is determined when the electrode is in the first influencing condition and that a second movement of the tag is determined when the electrode is in the second influencing condition; and controlling the functional property determination device such that the functional property is determined at least twice, one time from the first movement of the tag and another time from the second movement of the tag, in order to determine the influence of the electrode on the functional property of the moving object.

* * * * *